United States Patent
Breton et al.

(10) Patent No.: US 6,884,425 B2
(45) Date of Patent: *Apr. 26, 2005

(54) COSMETIC OR DERMATOLOGICAL COMPOSITION COMPRISING AN ASSOCIATION BETWEEN A COMPOUND OF THE N-ACYLAMINOAMIDE FAMILY AND AT LEAST ONE MATRIX METALLOPROTEINASE INHIBITOR

(75) Inventors: Lionel Breton, Versailles (FR); Yann Mahe, Morsang sur Orge (FR)

(73) Assignee: L'Oreal, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 10/179,934

(22) Filed: Jun. 26, 2002

(65) Prior Publication Data

US 2003/0044438 A1 Mar. 6, 2003

(30) Foreign Application Priority Data

Jun. 26, 2001 (FR) .............................. 01 08433

(51) Int. Cl.[7] .............................. A61K 7/00; A61K 7/42; A61K 38/00; A61K 31/66; A61K 31/19
(52) U.S. Cl. ........................ 424/401; 424/59; 514/119; 514/568; 514/2
(58) Field of Search ................... 424/401, 59; 514/119, 514/2, 568

(56) References Cited

U.S. PATENT DOCUMENTS 5,234,909 A 8/1993 Philippe

FOREIGN PATENT DOCUMENTS

| EP | 0 985 409 | 3/2000 | |
|----|-----------|--------|---|
| EP | 1 000 613 | 5/2000 | |
| EP | 1 090 628 | 4/2001 | |
| FR | 2 810 033 | 12/2001 | |
| JP | 2000-178163 | * 6/2000 | ............ A61K/7/48 |
| WO | WO 98/36742 | 8/1998 | |
| WO | WO 00/12467 | 3/2000 | |

OTHER PUBLICATIONS

U.S. Appl. No. 10/179,983, filed Jun. 26, 2002, Breton et al.
U.S. Appl. No. 10/179,934, filed Jun. 26, 2002, Breton et al.
U.S. Appl. No. 10/179,955, filed Jun. 26, 2002, Breton et al.
U.S. Appl. No. 10/179,984, filed Jun. 26, 2002, Breton et al.
Masayuki Nakamura et al.; "A Two–Step, One–Pot Synthesis of Diverse N–Pyruvoyl Amino Acid Derivatives Using the Ugi Reaction"; Bioorganic & Medicinal Chemistry Leters 10; (2000) 2807–2810, Dec. 18, 2000.

* cited by examiner

Primary Examiner—Shengjun Wang
(74) Attorney, Agent, or Firm—Oblon, Spivak, McClelland, Maier & Neustadt, P.C.

(57) ABSTRACT

A cosmetic or dermatological composition characterized in that it comprises an association between an elastase inhibitor compound of the N-acylaminoamide family and at least one metalloproteinase inhibiting compound.

20 Claims, No Drawings

COSMETIC OR DERMATOLOGICAL COMPOSITION COMPRISING AN ASSOCIATION BETWEEN A COMPOUND OF THE N-ACYLAMINOAMIDE FAMILY AND AT LEAST ONE MATRIX METALLOPROTEINASE INHIBITOR

This application claims foreign priority of France application 0108433, filed Jun. 26, 2001.

The present invention relates to the field of cosmetic or dermatological compositions. It relates to novel cosmetic or dermatological compositions comprising an association between an elastase inhibitor compound of the N-acylaminoamide family and at least one antagonist of the synthesis and/or of the release and/or the activity of matrix metalloproteinases. Such a composition is preferably adapted for improving the skin ageing and/or photoageing signs, which cutaneous signs are, as far as some of them are concerned, directly a result of a chronic micro-inflammatory process induced by repeated UV exposures.

The human skin consists in two compartments, i.e. a superficial compartment, the epidermis, and a deep compartment, the derma. The natural human epidermis mainly comprises three cell types, which are the keratinocytes, much in the majority, the melanocytes and the Langerhans cells. Each of such cell types contributes, by virtue of its own functions, to the essential part played in the skin organism.

The derma provides a solid support to the epidermis. It is also its nutritive element. It consists mainly in fibroblasts and one extracellular matrix, comprising, in its turn, mainly collagen, elastin and one substance, the so-called fundamental substance, formed with components synthetized by the fibroblast. It also comprises leukocytes, mastocytes or even tissue macrophages. It is also crossed by blood vessels and nervous fibres.

It is known that during a superficial skin stress, which can normally be from chemical, physical or bacterial origin, the keratinocytes from the epidermis superficial layers release biological mediators which are adapted to attract some of the skin infiltrating cells, which are themselves responsible for maintaining a transitory local irritation.

Biological mediators able to be produced by the thus-stressed keratinocytes include chemokines which are chemoattractive cytokines responsible for recruiting leukocytes on inflammatory sites, including the interleukin 8 (IL-8) which is more particularly responsible for recruiting neutrophils.

Such cells infiltrating into the irritated or attacked areas then release enzymes, amongst which me leukocyte elastase can be found. Under the action of such enzyme among others, the extracellular backing elastic fibres in connective tissue may be altered and thereby lead to a reduction of skin elasticity.

Further, it is also known that in synergy with cathepsin G, the leukocyte elastase may dissociate the epidermis integrity by enlarging the interkeratinocyte intercellular spaces.

Thus, in the long term, the sum of the superficial skin micro-stresses generated, for example, by a prolonged UV exposure or by irritating agents, can lead to a more or less accelerated loss of skin natural elasticity. The array formed by the elastic fibres in the underlying connective tissue and the extracellular spaces can then be progressively dismantled. This results in an accelerated ageing of the skin (wrinkled and/or less supple skin) with the derma elastic array being altered, as well as more accentuated wrinkles (deeper wrinkles).

Moreover, it is known that the derma resistance is also ensured by collagen fibres. Such fibres are made of fibrils sealed to each other, thereby forming more than ten types of various structures. The derma resistance is also due to an entanglement of collagen fibres which are packed one onto the other in all directions. The collagen fibres contribute to the skin and/or mucous membrane elasticity and tonicity.

The collagen fibres are continuously renewed, but such a renewal decreases over the age which also leads to the derma becoming thinner. This derma thinning is also due to pathological causes such as, for example, corticoid hormone hypersecretion, some pathologies or even vitamin deficiencies (which is the case of vitamin C in scorbutus). It is also recognized that extrinsic factors such as ultraviolet rays, tobacco or some treatments (Glucocorticoids, vitamin D and derivatives for example) also have an effect on the skin and the matrix protein rate thereof, more particularly collagen.

Though very resistant, the collagen fibres are sensitive to some enzymes, the so-called collagenases. An alteration of the collagen fibres leads to the skin having a soft and wrinkled appearance, against which the human being, preferring the appearance of a smooth and tense skin, has always tried to fight.

Moreover, in menopause period, the main variations relating to the derma are an alteration of the elastic tissue and a decrease of the collagen rate and the derma thickness. This leads, in the menopausal woman, to the skin and/or the mucous membranes becoming thinner. The woman then has the feeling of a "dry skin" or of a drawn skin and an increase of fine wrinkles and small surface wrinkles can also be noticed. The skin exhibits a rough aspect when touched. Finally, the skin exhibits a reduced suppleness.

Upon a (chemical, physical, bacterial or neurogeneous) skin stress, the keratinocytes release biological mediators (called chemoattractive factors) which are able to attract some inflammatory cells of the blood compartment towards the skin tissue. Such cells are responsible for generating, and subsequently, for maintaining a local irritation.

Amongst the chemoattractive factors able to be produced by the stressed keratinocytes, the interleukin 8 (IL-8) is more specifically responsible for recruiting the neutrophil polynuclears. Such cells infiltrating into the irritated or attacked areas then release enzymes, including the leukocyte elastase and other proteases (metalloproteinases, protease serines, etc).

Under the action of such enzyme, the extracellular backing elastic fibres in the connective tissue are altered. In synergy with the cathepsin G, the leukocyte elastase can also dissociate the epidermis integrity enlarging the interkeratinocyte intercellular spaces (Ludolph-Hauser et al. *Exp. Dermatol.* 1999 8(1) 46–52). The leukocyte elastase has recently been incriminated in maintaining eschars and in producing leg venous ulcers, through its fibronectin altering activity (Herrick S et al. *Lab. Invest* 1997(3) 281–288). The sum of the localized alteration micro-stresses (resulting, for example, from a prolonged exposure to the sun) can result in the long term in an accelerated loss of the natural elasticity in skin. The underlying connective tissue elastic fibre and the extracellular space array is then progressively dismantled. This accelerated alteration can be cumulated with the skin normal ageing process which is characterized by a higher sensitivity of the elastic fibres to the elastase action (Stadler R & Orfanos C E *Arch. Dermatol. Res.* 1978 262 (1) 97–111).

It is known in the state of the art that molecules can be brought in the skin tissue so as to slow down the alteration activity of the elastic fibres in the intercellular spaces.

But this not always satisfactory. Indeed, the fibril array is complex and numerous other enzyme activities can also degrade the elastin and the collagen and, as a consequence, dismantle and disorganize, through a site distinctive from the elastin, the collageno-elastic cutaneous array meshes. Such enzymes can include metalloproteinases and gelatinases adapted to degrade either the native collagen (like MMP-1, MMP-2 and MMP-14) or the denatured collagen in the form of gelatin (like MMP-9 and MMP-2).

The technical solution according to the invention is to bring, in addition to the regulating element of the elastase activity (the N-acylaminoamide derivative inhibiting the leukocyte elastase), one or more active ingredients being able to regulate as well the other enzyme activities interfering in the skin matrix array integrity, in the form of compositions.

Such a novel association can be used in care cosmetic compositions for areas exposed to the sun (scalp, body, face, lips), in care cosmetic compositions of ulcerated areas, in tooth-pastes or mouthwash lotions and, generally, in all the so-called "skin anti-ageing" cosmetic preparations, the objective of which is to slow down the chronobiological dismantling of backing tissues and the architecture of the skin matrix elements.

Consequently, the object of the invention is to provide a cosmetic or dermatological composition characterized in that it comprises an association between an elastase inhibiting compound of the N-acylaminoamide family and at least one metalloproteinase inhibitor.

It is understood by "metalloproteinase inhibitor" according to the invention meaning, an antagonist compound for the synthesis and/or the release and/or the activity of the matrix metalloproteinases.

Another object of the invention is to provide a cosmetic treating method for body or face skin, including the scalp, wherein a cosmetic composition such as defined hereunder is applied onto the skin.

In fact, it has been found that the compounds of the formula (I) showed an inhibiting activity of the elastase activity and that they can consequently be used for limiting and/or fighting against the elastic fibre alteration.

Therefore, they can be used in or for preparing a composition, the compounds or the composition being adapted to treat, in a preventive and/or curative way, the ageing skin signs.

The novel association of the N-acylaminoamides with at least one metalloproteinase inhibitor makes it possible to significantly reinforce the anti-ageing effect of the matrix tissue by addition of an effect both on the enzymes involved in the elastin degradation and on the enzymes involved in the collagen degradation.

According to the invention, the regulating element of the elastase activity (i.e. the N-Acylaminoamide derivative inhibitor of the enzyme activity of the leukocyte elastase), the {2-[acetyl-(3-trifluorometyl-phenyl)-amino]-3-methyl-butyrylamino}acetic acid is combined with one or more actives able to inhibit the activity, the synthesis or the release of the skin metalloproteinases.

The resulting composition is adapted to treat ageing disorders and/or to be more specifically designed to treat all the signs of skin ageing and/or photoageing.

More preferably, this novel association is used in care cosmetic preparations of the areas exposed to the sun (scalp, body, face, lips), and, generally, in all the so-called "skin anti-ageing" cosmetic preparations with the objective of slowing down the dismantling of the backing tissues and the architecture of the skin matrix elements.

Without being bound by any theory, the Applicant thinks that bringing, at the level of the skin superficial layer keratinocytes, compounds able to slow dawn the altering activity of the intercellular space elastic fibres, makes it possible to reduce this skin accelerated ageing phenomenon, resulting from superficial skin stresses and that the association of such compounds with a metalloproteinase inhibitor considerably reinforces their effects.

Preferred N-acylaminoamide Compounds

The compounds likely to be used in the present invention have therefore the following formula (I):

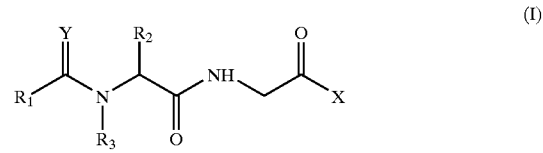

where:
the Y radical represents O or S,
the $R^1$ radical represents:
(i) a hydrogen atom,
(ii) a linear, branched or cyclic, saturated or unsaturated hydrocarbon radical having 1 to 18 carbon atoms,
optionally substituted by 1 to 5 groups, either identical or different, selected amongst —OH; —OR; —O—COR; —SH; —SR; —S—COR; —NH$_2$; —NHR; —NRR'; —NH—COR; Hal (halogen); —CN; —COOR; —COR; —P(O)—(OR)$_2$; —SO$_2$—OR; with R and R' representing, independently from each other, a linear, branched or cyclic, saturated or unsaturated hydrocarbon radical having 1 to 6 carbon atoms, optionally being halogenated or even perhalogenated;
said R and R' radicals being able to form together with N a carbon ring with 5 to 6 ring members optionally comprising further at least one heteroatom being selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical, having 1 to 6 carbon atoms, optionally being halogenated, even perhalogenated;
(iii) a radical selected amongst —OR; —NH$_2$; —NHR; —NRR'; —NH—COR; —COOR; —COR;
with R and R' representing, independently from each other, a linear, branched or cyclic, saturated or unsaturated hydrocarbon radical having 1 to 6 carbon atoms, optionally being halogenated, even perhalogenated;
said R and R' radicals being able to form together with N a carbon ring with 5 to 6 ring members optionally comprising, additionally, at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated, even perhalogenated;
the $R^2$ radical represents a linear, branched or cyclic, saturated or unsaturated hydrocarbon radical, with 1 to 18 carbon atoms, optionally substituted by 1 to 5 groups, either identical or different, selected amongst —OH; —OR; —O—COR; —SH; —SR; —S—COR;

—NH$_2$; —NHR; —NRR'; —NH—COR; Hal (halogen); —CN; —COOR; —COR; with R and R' representing, independently from each other, a hydrocarbon, straight, branched or cyclic, saturated or unsaturated radical, with 1 to 6 carbon atoms, optionally halogenated, or even perhalogenated; said R and R' radicals able to form together with N a carbon cycle with 5 to 6 chains optionally comprising, additionally, at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical, with 1 to 6 carbon atoms, optionally halogenated, even perhalogenated;

the R$^3$ radical represents a radical selected amongst those of the formulae (II) or (III):

-A-C$_6$H$_{(5-y)}$—B$_y$      (II)

—C$_6$H$_{(5-y')}$—B$_{y'}$      (III)

where:
y is an integer between 0 and 5 inclusive, and y' is an integer between 1 and 5 inclusive;

A is a linear or branched, saturated or unsaturated hydrocarbon divalent radical, with 1 to 18 carbon atoms, optionally being substituted by 1 to 5 groups, either identical or different, selected amongst —OH; —OR; —O—COR; —SH; —SR; —S—COR; —NH$_2$; —NHR; —NRR'; —NH—COR; Hal (halogen or even perhalogen); —CN; —COOR; —COR; —NO$_2$; —SO$_2$OR;

with R and R' representing, independently from each other, a linear, branched or cyclic, saturated or unsaturated hydrocarbon radical, with 1 to 6 carbon atoms, optionally being halogenated or even perhalogenated;

said R and R' radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated, even perhalogenated;

B is a linear or branched, saturated or unsaturated hydrocarbon radical having 1 to 18 carbon atoms, optionally substituted by 1 to 5 groups, either identical or different, selected amongst —OH; —OR; —O—COR; —SH; —SR; —S—COR; —NH$_2$; —NHR; —NRR'; —NH—COR; Hal (halogen or even perhalogen); —CN; —COOR; —COR; —NO$_2$; —SO$_2$OR;

with R and R' representing, independently from each other, a linear, branched or cyclic, saturated or unsaturated hydrocarbon radical having 1 to 6 carbon atoms, optionally being halogenated or even perhalogenated;

said R and R' radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon having 1 to 6 carbon atoms, optionally being halogenated or even perhalogenated;

the X radical is a radical selected amongst —OH; —OR$_4$; —NH$_2$; —NHR$_4$; —NR$_4$R$_6$; —SR$_4$; —COOR$_4$; —COR$_4$;

with R$_4$ and R$_5$ representing, independently from each other, a linear, cyclic or branched, saturated or unsaturated hydrocarbon radical having 1 to 6 carbon atoms, optionally substituted by 1 to 5 groups, identical or different, selected amongst —OH; —OR; —O—COR; —SH; —SR; —S—COR; —NH$_2$; —NHR; —NH—COR; -Hal (halogen, even perhalogen); —CN; —COOR; —COR; with R and R' representing, independently from each other, a linear, branched or cyclic, saturated or unsaturated hydrocarbon radical having 1 to 6 carbon atoms, optionally being halogenated or even perhalogenated; said R and R' radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated or even perhalogenated; said R$_4$ and R$_5$ radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated or even perhalogenated.

Are also included in such definition, the mineral or organic acid salts of said compounds, as well as the optical isomers thereof, in an isolated form or as a racemic mixture.

It is meant by a linear, cyclic or branched hydrocarbon radical, amongst others radicals of the alkyl, aryl, aralkyl, alkylaryl, alkenyl or alkynyl type.

The C$_6$H$_5$ group present in the R$_3$ radical should be understood as an aromatic cyclic group.

Preferably, the Y radical represents oxygen.

Preferably, the R$_1$ radical represents hydrogen or a linear or branched, saturated or unsaturated hydrocarbon radical having 1 to 12, more particularly 1, 2, 3, 4, 5 or 6 carbon atoms, optionally being substituted. Amongst others, the substituants can be selected amongst —OH; —OR; and/or —P(O)—(OR)$_2$ with R representing a linear, branched or cyclic, saturated or unsaturated hydrocarbon radical having 1 to 6 carbon atoms, optionally being halogenated, even perhalogenated.

More preferably, the R$_1$ radical represents a methyl, ethyl, propyl or isopropyl radical optionally substituted by a —OH or —P(O)—(OR)$_2$ group with R representing methyl, ethyl, propyl or isopropyl.

Preferably, the R$_2$ radical represents a linear, branched or cyclic, saturated or unsaturated hydrocarbon radical having 1 to 12, more particularly, 1, 2, 3, 4, 5 or 6 carbon atoms, optionally substituted.

Amongst others, the substituants can be selected amongst —OH and —OR with R representing a linear, branched or cyclic, saturated or unsaturated hydrocarbon radical having 1 to 6 carbon atoms, optionally being halogenated, even perhalogenated.

More preferably, the $R_2$ radical represents a methyl, ethyl, propyl, isopropyl, n-butyl, ter-butyl or isobutyl radical.

Preferably, the $R_3$ radical represents a radical of the formula —$C_6H_{(5-y')}$—$B_{y'}$ where y'=1, 2 or 3; or a radical of the formula -A-$C_6H_{(5-y)}$—$B_y$ where y=0, 1 or 2.

Preferably, A is a linear or branched, saturated or unsaturated hydrocarbon divalent radical having 1 to 12 carbon atoms, optionally substituted.

The substituants for A are preferably selected amongst -Hal (halogen, even perhalogen); —CN; —COOR; —$NO_2$; —$SO_2$—OR; with R representing a linear, branched or cyclic, saturated or unsaturated hydrocarbon radical having 1 to 6 carbon atoms, optionally being halogenated, even perhalogenated.

Preferably, B is a linear or branched, saturated or unsaturated hydrocarbon radical having 1 to 12 carbon atoms, optionally substituted.

The substituants for B are preferably selected amongst -Hal (halogen, even perhalogen); —CN; —COOR; —$NO_2$; —$SO_2$—OR; with R representing a linear, branched or cyclic, saturated or unsaturated hydrocarbon radical having 1 to 6 carbon atoms, optionally being halogenated, even perhalogenated.

More preferably, the $R_3$ radical is a group selected amongst one of the following formulae:

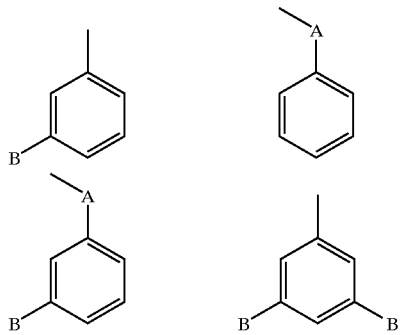

where A and B have the meanings as hereabove.

More particularly, the divalent A radical can be a methylene, an ethylene, a propylene.

The B radical is preferably a methyl, ethyl, propyl or isopropyl radical, substituted by one or more halogens, more particularly chlorine, bromine, iodine or fluorine, and more preferably completely halogenated (perhalogenated) such as perfluorinated. The most preferred one is in particular the perfluoromethyl radical (—$CF_3$).

More preferably, the X radical represents a radical selected amongst —OH or —$OR_4$ with $R_4$ representing a linear, cyclic or branched, saturated or unsaturated hydrocarbon radical having 1 to 6 carbon atoms, optionally substituted.

The substituants can be selected amongst —OH and —OR with R representing a linear, branched or cyclic, saturated or unsaturated hydrocarbon radical having 1 to 6 carbon atoms, optionally being halogenated, even perhalogenated.

More preferably, the X radical represents a radical selected amongst —OH, —$OCH_3$, —$OC_2H_5$, —O—$C_3H_7$ or —$OC_4H_9$.

The particularly preferred compounds include:
{2-[acetyl-(3-trifluoromethyl-phenyl)-amino]-3-méthyl-butyrylamino}acetic acid, {2-[acetyl-(3-trifluoromethyl-phenyl)-amino]-3-méthyl-butyrylamino}ethyl acetate,

[2-(acetyl-benzyl-amino)-3-méthyl-butyrylamino]acetic acid,

[2-(acetyl-benzyl-amino)-3-méthyl-butyrylamino]ethyl acetate, and

[2-{benzyl-[(diethoxy-phosphoryl)-acetyl]-amino}-3-méthyl-butyryl-amino]ethyl acetate.

The compounds according to the invention can be easily prepared by the man of the art based on its general knowledge. It is more particularly possible to react together a carboxylic acid, an aldehyde, an amino compound and an isonitrile, according to Ugi reaction.

Obviously, upon the synthesis of the compounds according to the invention and depending on the nature of the various radicals present on the starting compounds, the man of the art will make sure to protect some substituants so that they are not involved in the reaction sequence.

The compound quantity to be used in the compositions according to the invention can be easily determined by the man of the art, depending on the nature of the compound to be used, on the person to be treated and/or the desired effect. Generally, this amount can range from 0.00001 to 20% by weight based on the total weight of the composition, preferably 0.0001 to 5% by weight.

The compounds of the formula (I) can normally be used, in a composition comprising a physiologically acceptable medium, including in a cosmetic or pharmaceutical composition thus additionally comprising a cosmetically or pharmaceutically acceptable medium.

The physiologically acceptable medium wherein the compounds according to the invention can be used, as well as the components thereof, their amount, the galenic form and its preparation mode, can be selected by the man of the art based on its general knowledge depending on the desired composition type.

Generally, such a medium can be anhydrous or aqueous. It can also comprise an aqueous phase and/a fatty phase.

Preferred Metalloproteinase Inhibitors

It is meant by "metalloproteinase inhibitor" according to the invention any molecule and/or vegetable or bacterial extract showing an inhibiting activity on the skin metalloproteinases.

Metalloproteinases are more particularly described in Y. HEROUY et al., *European Journal of Dermatology*, n° 3, vol. 10, April–May 2000, pp. 173–180.

The metalloproteinase family thus comprises several well defined groups based on their similarities in term of structure and substrate specificity (see Woessner J. F., *Faseb Journal*, vol. 5, 1991, 2145). Such groups can include collagenases adapted to degrade the fibril collagens (MMP-1 or interstitial collagenase, MMP8 or neutrophil collagenase, MMP-13 or collagenase 3, MMP-18 or collagenase 4), gelatinases degrading the type IV collagen or any form of denatured collagen (MMP-2 or gelatinase A (72 kDa), MMP-9 or gelatinase B (92 kDa)), stromelysins (MMP-3 or stromelysin 1, MMP-10 or stromelysin 2, MMP-11 or stromelysin 3), the broad activity spectrum of which addresses proteins of the extracellular matrix such as glycoproteins (fibronectin, laminin), proteoglycans, etc., matrilysin (MMP-7), metalloelastase (MMP-12) or even membrane metalloproteinases (MMP-14, MMP-15, MMP-16 and MMP-17).

The metalloproteinases (MMPs) are the members of a proteolytic enzyme family (endoproteases) having a zinc atom coordinated with 3 cystein residues and with a methionine in their active site and degrading macromolecular components of the extracellular matrix and basal lamellae at a neutral pH (collagen, elastin, etc.). Very widely spread in the living world, such enzymes are present, but weakly expressed, in normal physiological situations such as organ growth and tissue renewal.

Their overexpression in man and their activation are however bound to numerous processes involving the matrix destruction and restructuration. This leads, for example, to an uncontrolled resorption of the extracellular matrix.

Thus, a prolonged exposure to ultraviolet radiations, more particularly to ultraviolet rays of the type A and/or B, has the effect of stimulating the collagenase expression, particularly of the MMP-1. This is one of the components of the photoinduced skin ageing. Moreover, it is known that the activity of MMP-1, MMP-2 and MMP-9 increases over the age and that such an increase contributes, with the cell growth slowing down, to the skin chronological ageing (WO 98/36742).

The metalloproteinases are produced and secreted under an inactive form (pro-enzyme). Such inactive forms, so-called zymogens, are then activated in the extracellular environment through elimination of a propeptid area. The members of this family can activate one another. The MMP activity regulation occurs therefore at the level of the gene expression (transcription and translation), at the level of the zymogen form activity, or at the level of the local control of the active forms.

The natural regulators of the MMP activity are the tissue inhibitors of metalloproteinases or TIMPs (tissue inhibitors of metalloproteinases). However, the expression of the MMPs is also modulated by the growth factors, the cytokines, the oncogenic products (ras, jun) or even the matrix components.

It is meant by metalloproteinase inhibitor according to the invention, any molecule being able to regulate the MMP activity either at the level of the gene expression (transcription and translation), either at the level of the activation of the MMP zymogen form activity, or also at the level of the local control of the active forms.

More preferably, a composition according to the invention is characterized in that the metalloproteinase inhibitor is selected amongst an inhibitor of a metalloproteinase selected amongst MMP-1, MMP-2, MMP-3, MMP-7, MMP-9, MMP-11, MMP-12, MMP-13, MMP-14, MMP-15, MMP-16 and MMP-17. The metalloproteinase inhibitor according to the invention can be a natural inhibitor of metalloproteinases, particularly a tissue inhibitor of the metalloproteinases (TIMP) such as peptides known in the prior art under the names TIMP-1, TIMP-2, TIMP-3 and TIMP-4 (Woessner J. F., Faseb Journal, 1991).

Alternatively, the metalloproteinase inhibitors suitable for use in the present invention may be MMP-1 inhibitors from natural or synthetic origin. It is meant by "natural origin", the metalloproteinase inhibitor in a pure state or in a solution at various concentrations, obtained by means of various exacting methods from an element, generally a plant, from natural origin. It is meant by "synthetic origin" the metalloproteinase inhibitor in a pure state or in a solution at various concentrations, obtained through chemical synthesis.

The metalloproteinase inhibitor can also be a natural extract containing ursolic acid or carotenoids or vitamin C or isoflavones like the genistein known for its metalloproteinase inhibiting activity (U.S. Pat. No. 6,130,254).

According to a preferred embodiment of the invention, a metalloproteinase inhibitor from natural origin is used, such as lycopene or an isoflavone. The lycopene activity on the metalloproteinases have been disclosed in Patent Application EP-A-1090628.

According to another preferred embodiment, the metalloproteinase inhibitor is a MMP-1 metalloproteinase transcriptional inhibitor, such as retinol or the derivatives thereof, retinoic acid and the derivatives thereof. The inhibitors to be associated with can also be selected amongst retinoic acid and the derivatives thereof, adapalene or also analogous peptides and/or the derivatives of Batimastat ((BB 94)=[4-(N-hydroxyamino)-2R-isobutyl-3S-(thiophen-2-ylthiomethyl)-succinyl]-L-phenylalanine-N-methylamide), of Marimastat ((BB 2516)=[2S-[N4(R*), 2R*,3S]]-N4[2,2-dimethyl-1-[(methylamino)carbonyl] propyl]-N1,2-dihydroxy-3-(2-methyl-propyl) butanediamide) sold by the British Biotech corporation or also natural biological inhibitors such as the tissue inhibitors of metalloproteinases (TIMPs), as well as structural and/or functional analogs, even also inducers for synthesis and/or release of such natural inhibitors. Sunscreens, by virtue of an indirect action on metalloproteinase transcription et/or synthesis, are also useful according to the invention.

More preferably, a composition according to the invention will contain retinol as a metalloproteinase inhibitor.

Ideally, it will be possible to use such a novel association in care cosmetic preparations for sun exposed areas (scalp, body, face, lips) and, generally, in all the so-called "skin anti-ageing" cosmetic preparations with the objective of slowing down the chronobiological dismantling of the backing tissues and the architecture of the skin matrix elements.

The metalloproteinase inhibitor preferably represents $10^{-12}$ to 5%, more preferably $10^{-10}$ to 2% of the total weight of the composition. Obviously, if the metalloproteinase inhibitor is present in the form of a solution containing a plant extract, the man of the art will be able to adjust such a solution amount in the composition of the invention, so as to obtain the expected effect on the activity and/or the synthesis and/or the release of metalloproteinases.

The association of at least one N-acylaminoamide compound and at least one metalloproteinase inhibitor can be used, more particularly, alone or in a mixture, in a composition comprising a physiologically acceptable medium, in particular in a cosmetic or pharmaceutical composition which, therefore, comprises a cosmetically or pharmaceutically acceptable medium.

The physiologically acceptable medium in which the compounds according to the invention can be used, as well as the components thereof, their amount, the galenic form of the composition and its preparation mode, can be selected by the man of the art on the basis of its general knowledge depending on the type of the desired composition.

Generally, such a medium can be anhydrous or aqueous. It can thus comprise an aqueous phase and/or a fatty phase.

For applying onto the skin, the composition can have the form in particular of an aqueous or an oily solution; of a dispersion of the lotion or serum type, of emulsions of liquid or semi-liquid consistency of the milk type obtained through dispersion of a fatty phase into an aqueous phase (O/W) or reversely (W/O); of suspensions or emulsions of a soft consistency of the cream type or aqueous or anhydrous gel type; of microcapsules or microparticles; of vesicular dispersions of the ionic and/or non ionic type.

For applying on the hair, the composition can be in the form of aqueous, alcoholic or hydroalcoholic solutions; in the form of creams, gels, emulsions, foams; in the form of aerosol compositions comprising a pressurized propellant as well.

When the composition is in an aqueous form, in particular in an aqueous dispersion, emulsion or solution, it can comprise an aqueous phase, which may comprise water, flower water and/or mineral water.

Said aqueous phase can additionally comprise alcohols such as $C_1$–$C_6$ monoalcohols and/or polyols such as glycerol, butyleneglycol, isoprene glycol, propyleneglycol, polyethyleneglycol.

When the composition according to the invention is in the form of an emulsion, it can optionally additionally comprise a surfactant, preferably in an amount ranging from 0.01 to 30% by weight based on the total weight of the composition. The composition according to the invention can also comprise at least one co-emulsifier which can be selected amongst oxyethylenated sorbitan monostearate, fatty alcohols such as stearyl alcohol or cetyl alcohol, or esters of fatty acids and polyols such as glyceryl stearate.

The composition according to the invention can also comprise a fatty phase, in particular made of fatty bodies liquid at 25° C., such as oils from animal, vegetable, mineral or synthetic origin, either volatile or not, fatty bodies solid at 25° C. such as waxes from animal, vegetable, mineral or synthetic origin; of pasty fatty bodies; of gums; and the mixtures thereof.

The volatile oils are generally oils having, at 25° C., a saturating vapor tension at least equal to 0.5 millibar (50 Pa).

Are included amongst the fatty phase components:

cyclic volatile silicones having 3 to 8 silicon atoms, preferably 4 to 6, cyclocopolymers of the dimethylsiloxane/methylalkylsiloxane type, linear volatile silicones with 2 to 9 silicon atoms, hydrocarbon volatile oils, such as isoparaffins and, more particularly, isododecane and fluorinated oils, poly($C_1$–$C_{20}$)alkylsiloxanes and, more particularly, those with trimethylsilyl end groups, amongst which linear polydimethylsiloxanes and alkylmethylpolysiloxanes such as cetyldimethicone (CTFA name), silicones modified by aliphatic and/or aromatic groups, optionally fluorinated, or by functional groups such as hydroxyl, thiol and/or amine groups, phenylated silicone oils, oils from animal, vegetable or mineral origin, in particular animal or plants oils made of esters of fatty acids and polyols, in particular liquid triglycerids, for example sunflower, corn, soya, marrow, grape seed, sesame, hazelnut, apricot, almond, or avocado oils; fish oils, glycerol tricaprocaprylate, or plant or animal oils having the formula $R_1COOR_2$, where $R_1$ represents the residue of a superior fatty acid having 7 to 19 carbon atoms and $R_2$ represents a branched hydrocarbon chain having 3 to 20 carbon atoms, for example Purcellin oil; paraffin oil, liquid paraffin, perhydrosqualene, wheatgerm, calophyllum, sesame, macadamia, grape seed, colza, copra, arachis, palm, castor, jojoba, olive or cereal germ oils; fatty acid esters; alcohols; acetylglycerides; octanoates, decanoates or ricinoleates from alcohols or polyalcohols; fatty acid triglycerids; glycerids;

fluorinated and perfluorinated oils;

silicone gums;

waxes from animal, vegetable, mineral or synthetic origin, such as microcrystalline waxes, paraffin, petrolatum, liquid paraffin, ozokerite, Montan wax; beewax, lanolin, and the derivatives thereof;

Candelilla, Ouricury and Japan waxes, cocobutter, cork fibre or sugar cane waxes; hydrogenated oils solid at 25° C., ozokerites, fatty esters and glycerides solid at 25° C.; polyethylene waxes and waxes obtained through Fischer-Tropsch synthesis; hydrogenated oils solid at 25° C.; lanolins; fatty esters solid at 25° C.; silicone waxes; fluorinated waxes.

As it is known, the composition according to the invention can comprise the usual builders in the field being involved, such as hydrophilic or lipophilic gelling agents, hydrophilic or lipophilic additives, actives, in particular hydrophilic or lipophilic cosmetic or pharmaceutical actives, preservatives, antioxidants, solvents, perfumes, fillers, pigments, nacres, UV filters, odor absorbers and colorants. Such builders, depending on their nature, can be introduced into the fatty phase, into the aqueous phase and/or into lipid spherules.

The nature and the amount of such builders can be selected by the man of the art, based on its general knowledge, so as to obtain the desired presentation form for the composition. Anyway, the man of the art will make sure to select all the optional complementary compounds and/or their amount, so that the advantageous properties of the composition according to the invention are not, or substantially not, altered by the contemplated addition.

The cosmetic or pharmaceutical compositions according to the invention can, in particular, have the form of a composition designed for caring and/or treating ulcerated areas or which have been subjected to a cutaneous stress or microstress, in particular generated by an exposure to the UV and/or the contact with an irritating product.

Accordingly, the compositions according to the invention can, in particular, exhibit the form of:

a care, treatment, cleaning or protection product for the face or the body skin, including the scalp, such as a (day, night, hydrating) care composition for the face or the body; an anti-wrinkle or anti-ageing composition for the face; a mating composition for the face; a composition for the irritated skins; a make-up removing composition; a body milk, in particular being hydrating optionally an after-sun body milk;

a sun protective, artificial sun tanning (self-tanning) or after-sun care composition;

a capillary composition, more particularly a sun protective cream or gel; a scalp care composition, including an hair restoring or hair growth composition; an anti-parasitic shampoo;

a face skin, body or lip makeup product, such as a foundation cream, a tinted cream, a cheek or eye-lid makeup product, a free or compact powder, an anti eye-ring stick, a concealing stick, a lipstick, a lip care product; and a mouth hygiene product, such as a tooth-paste or a mouthwash lotion.

The compositions according to the invention find a preferred application as a composition for face skin care, of the anti-wrinkle or anti-ageing type and as a sun protective or an after-sun composition.

The object of the present invention is also to provide a method comprising the steps of cosmetically treating the body or the face skin, in particular, the scalp, wherein a cosmetic composition is applied onto the skin, comprising an association between a compound of the N-acylaminoamide family and at least a metalloproteinase inhibitor, leaving it in contact and optionally rinsing.

The cosmetic treatment method according to the invention can be applied in particular by applying cosmetic compositions such as defined hereabove, according to the usual use technique of said compositions. For example: application of creams, gels, serums, lotions, make-up removing milks or anti-sun compositions on the skin or on dry hair; application of a scalp lotion on wet hair, application of tooth-paste on the gums.

The invention is illustrated in further detail in the following examples.

EXAMPLE 1

Preparation of {2-[acetyl-(3-trifluoromethyl-phenyl)-amino]-3-méthyl-butyrylamino}ethyl acetate of the formula:

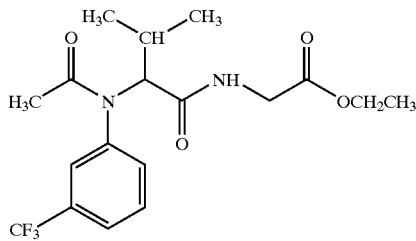

0.63 ml isobutyraldehyde and 1 ml trifluoromethylamine (1.15 eq) are mixed in 15 ml methanol under stirring. It is left to react for 15 minutes at 20° C., thereafter 0.46 ml acetic acid are added (1.15 eq) and it is left to react for 10 minutes at 20° C. Then 0.8 ml 95% ethyl isocyanoacetate (1 eq) are added and left to react for 48 hours at 20° C.

The reaction medium is concentrated using a rotovapor and the residue is purified on a silica column (eluant: heptane: 3/ethyl acetate: 7; Rf=0.5).

2.45 g of a compound in the form of a waxy solid are obtained, whence a 91% yield.

NMR$^1$H (200 MHz; CDC13) δ ppm: 0.9 (6H; q), 1.3 (3H; t), 1.8 (3H; s), 2.3 (1H; m), 4.0 (2H; q), 4.2 (2H; q), 4.4 (2H; d), 7.3 (1H; t), 7.5 (4H; m).

EXAMPLE 2

Preparation of {2-[acetyl-(3-trifluoromethyl-phenyl)-amino]-3-méthyl-butyrylamino}acetic acid of the formula:

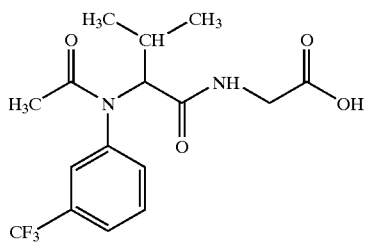

2 g of the compound prepared according to example 1 are solubilized in 30 ml acetone. 30 ml 2N sodium hydroxyde are added and left to react for 6 hours at 20° C. The reaction medium is concentrated using a rotovapor. The residual aqueous phase is acidified at pH 2 adding concentrated HCl and then extracted with $CH_2Cl_2$.

The organic phase is dry concentrated after drying on sodium sulfate.

A residue is obtained which is solubilized with a base water mixture at 10% ethanol and then again acidified with concentrated HCl at pH 2. A new extraction by $CH_2Cl_2$ is performed, the organic phase is dried on sodium sulfate, filtered and dry concentrated under vacuum in a rotovapor.

1.3 g of a compound are obtained in the form of a slight light brown solid, whence a 70% yield.

NMR$^1$H (200 MHz; DMSO) δ ppm : 0.9 (6H; q), 3.7 (2H; m), 1.8 (4H; m), 4.8 (2H; d), 7.6 (4H; q), 8.4 (1H; t), 12.5 (1H; s).

EXAMPLE 3

The anti-elastasic activity of compounds according to the invention is determined in vitro compared to the human leukocyte elastase (ELH).

The test is performed in the following way:

A Me-OSAAPV-p-NA (méthyl-O-succinate alanine alanine proline valine-p-nitroaniline) substrate, onto which ELH (40 milli-units per ml) and 0.1% of the compound to be tested are applied, is left for incubating at 37° C. for 60 minutes.

Thereafter, the % inhibition of the control elastase activity is determined by spectrophotometry, The tested compounds are the following:
Compound A: {2-[acetyl-(3-trifluoromethyl-phenyl)-amino]-3-méthyl-butyryl-amino}acetic acid,
Compound B: (2-{benzyl-[(diéthoxy-phosphoryl)-acetyl]-amino}-3-méthyl-butyryl-amino)ethyl acetate,
Compound C: [2-(acetyl-benzyl-amino)-3-méthyl-butyrylamino]acetic acid,
Compound D: [2-(acetyl-benzyl-amino)-3-méthyl-butyrylamino]ethyl acetate.

The following results are obtained:

| Compound (concentration: 0.1%) | % Inhibition of the control elastase activity |
|---|---|
| Compound A | 67% |
| Compound B | 17% |
| Compound C | 20% |
| Compound D | 13% |

The same way, the % inhibition of the control elastase activity is determined for compound A, at various concentrations.

The following results are obtained:

| Compound A concentration | % Inhibition of the control elastase activity |
|---|---|
| 0.01% | 53% |
| 0.05% | 50% |
| 0.1% | 68% |
| 0.2% | 68% |

Compound A therefore generates a strong inhibition of the elastase activity, even in a small amount.

EXAMPLE 4

The ex vivo activity of example 2 compound has been evaluated on surviving human skins treated by a human leukocyte elastase (ELH).

The test is performed the following way.

Fresh human skin cuts from two different donors are treated for 2 hours, at 20° C., by 20 μl of a buffer solution (pH 7.4) optionally comprising 10 μg/ml ELH and optionally 0.1% of the compound to be tested, optionally previously put in solution in ethanol.

The elastic fibres are coloured in blue using catechin (+) and quantified morphometrically using a computer assisted image analysis. The average derma surface percentage occupied by elastic fibres is evaluated this way.

The following results are obtained:

|  | % Surface occupied by elastic fibres | |
| --- | --- | --- |
|  | Skin 1 | Skin 2 |
| Control (untreated skin) | 12.7% | 15.25% |
| ELH treated skin | 4.85% | 6.85% |
| ELH treated skin + example 2 compound | 13.95% | 11.85% |

It is therefore found out that the compound according to the invention generates a skin significant protection against the destruction of elastic fibres induced by elastase.

EXAMPLE 5

The ex vivo activity of example 2 compound has been evaluated on surviving human skins treated by a human leukocyte elastase (ELH).

The test is performed the following way:

Fragments of normal human skin from three different donors are deposited in inserts positioned in culture wells. Culture medium added with antibiotics is added in the bottom of the wells. A pass is performed through slow diffusion between the two compartments via a porous membrane (pore size: 12 $\mu$m).

The culture medium is renewed every three days.

On the skin fragments, optionally 0.5 $\mu$g ELH per ml culture medium are added.

5 $\mu$l of the compound to be tested are also added every two days, previously put in solution at 0.2% by weight in ethanol.

The skins are kept surviving for 10 days at 37° C.

The elastic fibres are coloured in blue using catechin (+) and quantified morphometrically using a computer assisted image analysis. The average derma surface percentage occupied by elastic fibres is evaluated this way.

The following results are obtained:

|  | % Surface occupied by elastic fibres |
| --- | --- |
| Control (untreated skin) | 7.4% |
| ELH treated skin | 5.1% |
| ELK treated skin + example 2 compound | 7.1% |

It is therefore found out that the compound according to the invention generates a significant skin protection against the destruction of elastic fibres induced by the elastase.

EXAMPLE 6

The activity of the example 2 compound has been evaluated on surviving human skins irradiated by UVA (8 J/cm$^2$).

The test is performed the following way.

Fragments of normal human skin from four different donors are deposited in inserts positioned in culture wells. Culture medium added with antibiotics is added in the bottom of the wells. A pass is performed through slow diffusion between the two compartments via a porous membrane (pore size: 12 $\mu$m).

The culture medium is renewed every three days.

On the skin fragments, every two days, 5 $\mu$l of a 0.2% solution of the compound to be tested are added, in solution in ethanol.

The skins are kept surviving for 7 days at 37° C.

The skins are irradiated once at 8 J/cm$^2$ (RMX-3W Vilbert-Lourmat lamp).

The elastic fibres are coloured in blue using catechin (+) and quantified morphometrically using a computer assisted image analysis. The average derma surface percentage occupied by elastic fibres is evaluated this way.

The following results are obtained:

|  | Elastic fibres morphometric analysis (superficial derma) | Collagen morphometric analysis (superficial derma) |
| --- | --- | --- |
| Untreated skin | 6.75% | 87% |
| UVA treated skin (8 J/cm$^2$) | 3.9% | 81% |
| UVA treated skin (8 J/cm$^2$) + compound | 6.8% | 92% |

It is found out that the compound according to the invention does have an activity towards the destruction of elastic fibres in the UVA irradiated skin superficial derma.

This compound also exhibits an adequate effect on the collagen protection.

EXAMPLE 7

Composition for Topic Application

The following emulsion is prepared conventionally (% by weight):

| | |
| --- | --- |
| Compound from example 1 | 1% |
| Retinol | 0.1% |
| Propylene glycol isostearate | 13% |
| Polyethylene glyocl (8 OE) | 5% |
| Propylene glycol | 3% |
| Pentylene glycol | 3% |
| Glyceryl stearate and polyethylene glycol stearate (100 OE) | 5% |
| Oxyethylenated (20 OE) sorbitan monostearate | 0.5% |
| Oxypropylenated (20 OE) oxyethylenated (5 OP) cetyl alcohol | 1% |
| Gelling agents | 0.5% |
| C$_{12}$–C$_{15}$ alkyl benzoates | 4% |
| Ethanol | 3% |
| Sodium hydroxide | 0.12% |
| Preservatives | qs |
| Water | qsp 100% |

EXAMPLE 9

Face Care Cream

The following oil-in-water emulsion is prepared conventionally (% by weight):

| | |
| --- | --- |
| Example 2 compound | 1% |
| Lycopene (in the form of Lycomato ® at 10% of lycopene in a tomato oleoresin sold by Lycored ®) | 0.001% |
| Glycal stearate | 2% |
| Polysorbate 60 (Tween 6O ® sold by ICI corporation) | 1% |

-continued

| | |
|---|---|
| Stearic acid | 1.4% |
| Triethanolamine | 0.7% |
| Carbomer | 0.4% |
| Shea butter liquid fraction | 12% |
| Perhydrosqualene | 12% |
| Antioxidant | qs |
| Perfume | qs |
| Preservative | qs |
| Water | qsp 100% |

EXAMPLE 9

Face Milk

The following milk is prepared according to the conventional way (% by weight):

| | |
|---|---|
| Liquid paraffin | 7% |
| Genistein | 0.2% |
| Example 2 compound | 1% |
| Glyceryl monostearate, polyethylene glycol stearate (100 OE) | 3% |
| Carboxyvinyl polymer | 0.4% |
| Stearyl alcohol | 0.7% |
| Soya protein | 3% |
| NaOH | 0.4% |
| Preservative | qs |
| Water | qsp 100% |

EXAMPLE 10

Hair Lotion

The following lotion is prepared conventionally (% by weight):

| | |
|---|---|
| Example 1 compound | 1% |
| Retinol | 0.01% |
| Propylene glycol | 23% |
| Ethanol | 55% |
| Water | qsp 100% |

This lotion can be applied onto the scalp of alopecic people for preventing the UV effects, before and/or after sun exposure.

EXAMPLE 11

Hair Restoring Lotion

The following lotion is prepared conventionally (% by weight):

| | |
|---|---|
| Example 2 compound | 1% |
| Lycopene (in the form of Lycomato ® at 10% of lycopene in a tomato oleoresin sold by Lycored ®) | 0.0001% |
| Propylene glycol | 23% |
| Ethanol | 55% |
| Aminexil | 1.5% |
| Water | qsp 100% |

This hair restoring lotion can be applied onto the scalp of alopecic people.

What is claimed is:

1. A composition comprising an N-acylaminoamide elastase inhibitor and at least one metalloproteinase inhibitor, wherein the elastase inhibitor is a compound of the formula (I):

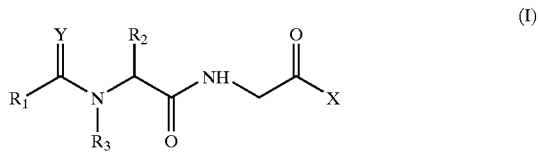

where
the Y radical represents O or S,
the $R_1$ radical represents
(i) a hydrogen atom,
(ii) a linear, branched or cyclic, saturated or unsaturated hydrocarbon radical having 1 to 18 carbon atoms,
optionally substituted by 1 to 5 groups, either identical or different, selected from the group consisting of —OH; —OR; —O—COR; —SH; —SR; —S—COR; —NH$_2$; —NHR; —NRR'; —NH—COR; halogen; —CN; COOR; —COR; —P(O)—(OR)$_2$; —SO$_2$—OR; with R and R' representing, independently from each other, a linear, branched or cyclic, saturated or unsaturated hydrocarbon radical having 1 to 6 carbon atoms, optionally being halogenated;
said R and R' radicals being able to form together with N a carbon ring with 5 to 6 ring members optionally further comprising at least one heteroatom being selected from the group consisting of O, N and S in the ring and/or optionally substituted by 1 to 5 groups, identical or different, selected from the group consisting of —OH; —OR"; —O—COR"; —SH; —SR"; —S—COR"; —NH$_2$; —NHR"; —NH—COR"; halogen; —CN; —COOR"; and —COR"; with R" representing a linear, branched or cyclic, saturated or unsaturated hydrocarbon radical, having 1 to 6 carbon atoms, optionally being halogenated;
(iii) a radical selected from the group consisting of —OR; —NH$_2$; —NHR; —NRR'; —NH—COR; —COOR; —COR;
with R and R' representing, independently from each other, a linear, branched or cyclic, saturated or unsaturated hydrocarbon radical having 1 to 6 carbon atoms, optionally being halogenated;
said R and R' radicals being able to form together with N a carbon ring with 5 to 6 ring members optionally comprising, additionally, at least one heteroatom selected from the group consisting of O, N and S in the ring and/or optionally substituted by 1 to 5 groups, identical or different, selected from the group consisting of —OH; —OR"; —O—COR"; —SH; —SR"; —S—COR"; —NH$_2$; —NHR"; —NH—COR"; halogen; —CN; —COOR"; and —COR"; with R" representing a linear, branched or cyclic, saturated or unsaturated hydrocarbon radical having 1 to 6 carbon atoms, optionally being halogenated;
the $R^2$ radical represents a linear, branched or cyclic, saturated or unsaturated hydrocarbon radical, with 1 to 18 carbon atoms, optionally substituted by 1 to 5 groups, either identical or different, selected from the group consisting of —OH; —OR; —O—COR; —SH; —SR; —S—COR; —NH$_2$; —NHR; —NRR'; —NH—

COR; halogen; —CN; —COOR; and —COR; with R and R' representing, independently from each other, a hydrocarbon, linear, branched or cyclic, saturated or unsaturated radical, with 1 to 6 carbon atoms, optionally halogenated; said R and R' radicals able to form together with N a carbon cycle with 5 to 6 chains optionally comprising, additionally, at least one heteroatom selected from the group consisting of O, N and S in the ring and/or optionally substituted by 1 to 5 groups, identical or different, selected from the group consisting of —OH; —OR"; —O—COR"; —SH; —SR"; —S—COR"; —NH$_2$; —NHR"; —NH—COR"; halogen; —CN; —COOR"; and —COR"; with R" representing a linear, branched or cyclic, saturated or unsaturated hydrocarbon radical, with 1 to 6 carbon atoms, optionally halogenated the $R^3$ radical represents a radical selected from formulae (II) or (III)

(II)

(III)

where y is an integer between 0 and 5 inclusive, and y' is an integer between 1 and 5 inclusive;

A is a linear or branched, saturated or unsaturated hydrocarbon divalent radical, with 1 to 18 carbon atoms, optionally being substituted by 1 to 5 groups, either identical or different, selected from the group consisting of —OH; —OR; —O—COR; —SH; —SR; —S—COR; —NH$_2$; —NHR; —NRR'; —NH—COR; halogen; —CN; —COOR; —COR; —NO$_2$; and —SO$_2$OR;

with R and R' representing, independently from each other, a linear, branched or cyclic, saturated or unsaturated hydrocarbon radical, with 1 to 6 carbon atoms, optionally being halogenated;

said R and R' radicals being able to form together with N a carbon ring with 5 to 6 ring members optionally comprising further at least one heteroatom selected from the group consisting of O, N and S in the ring and/or optionally substituted by 1 to 5 groups, identical or different, selected from the group consisting of —OH; —OR"; —O—COR"; —SH; —SR"; —S—COR"; —NH$_2$; —NHR"; —NH—COR"; halogen; —CN; —COOR"; and —COR"; with R" representing a linear, branched or cyclic, saturated or unsaturated hydrocarbon radical having 1 to 6 carbon atoms, optionally being halogenated;

B is a linear or branched, saturated or unsaturated hydrocarbon radical having 1 to 18 carbon atoms, optionally substituted by 1 to 5 groups, either identical or different, selected from the group consisting of —OH; —OR; —O—COR; —SH; —SR; —S—COR; —NH$_2$; —NHR; —NRR'; —NH—COR; halogen; —CN; —COOR; —COR; —NO$_2$; and —SO$_2$OR;

with R and R' representing, independently from each other, a linear, branched or cyclic, saturated or unsaturated hydrocarbon radical having 1 to 6 carbon atoms, optionally being halogenated;

said R and R' radicals being able to form together with N a carbon ring with 5 to 6 ring members optionally comprising further at least one heteroatom selected from the group consisting of O, N and S in the ring and/or optionally substituted by 1 to 5 groups, identical or different, selected from the group consisting of —OH; —OR"; —O—COR"; —SH; —SR"; —S—COR"; —NH$_2$; —NHR"; —NH—COR"; halogen; —CN; —COOR"; and —COR"; with R" representing a linear, branched or cyclic, saturated or unsaturated hydrocarbon having 1 to 6 carbon atoms, optionally being halogenated;

the X radical is a radical selected from the group consisting of —OH; —OR$_4$; —NH$_2$; —NHR$_4$; —NR$_4$R$_5$; —SR$_4$; —COOR$_4$; and —COR$_4$;

with R$_4$ and R$_5$ representing, independently from each other, a linear, cyclic or branched, saturated or unsaturated hydrocarbon radical having 1 to 6 carbon atoms, optionally substituted by 1 to 5 groups, identical or different, selected from the group consisting of —OH; —OR; —O—COR; —SH; —SR; —S—COR; —NH$_2$; —NHR; —NH—COR; halogen; —CN; —COOR; —COR; with R and R' representing, independently from each other, a linear, branched or cyclic, saturated or unsaturated hydrocarbon radical having 1 to 6 carbon atoms, optionally being halogenated; said R and R' radicals being able to form together with N a carbon ring with 5 to 6 ring members optionally comprising further at least one heteroatom selected from the group consisting of O, N and S in the ring and/or optionally substituted by 1 to 5 groups, identical or different, selected from the group consisting of —OH; —OR"; —O—COR"; —SH; —SR"; —S—COR"; —NH$_2$; —NHR"; —NH—COR"; halogen; —CN; —COOR"; and —COR"; with R" representing a linear, branched or cyclic, saturated or unsaturated hydrocarbon radical having 1 to 6 carbon atoms, optionally being halogenated; said R$_4$ and R$_5$ radicals being able to form together with N a carbon ring with 5 to 6 ring members optionally comprising further at least one heteroatom selected from the group consisting of O, N and S in the ring and/or optionally substituted by 1 to 5 groups, identical or different, selected from the group consisting of —OH; —OR"; —O—COR"; —SH; —SR"; —S—COR"; —NH2; —NHR"; —NH—COR"; halogen; —CN; —COOR"; and —COR"; with R" representing a linear, branched or cyclic, saturated or unsaturated hydrocarbon radical having 1 to 6 carbon atoms, optionally being halogenated the mineral or organic acid salts thereof, the optical isomers thereof, in an isolated form or as a racemic mixture.

2. A composition according to claim 1, wherein the compound of formula (I) is such that:

the Y radical represents oxygen, and/or the R$_1$ radical represents hydrogen or a linear or branched, saturated or unsaturated hydrocarbon radical having 1 to 12 carbon atoms, optionally substituted, and/or the R$_1$ substituents being selected from the group consisting of —OH; —OR; and —P(O)—(OR)$_2$ with R representing a linear, branched or cyclic, saturated or unsaturated hydrocarbon radical having 1 to 6 carbon atoms, optionally being halogenated; and/or the R$_2$ radical represents a linear, branched or cyclic, saturated or unsaturated hydrocarbon radical having 1 to 12, carbon atoms, optionally substituted, and/or the R$_2$ substituents being —OH or —OR with R representing a linear, branched or cyclic, saturated or unsaturated hydrocarbon radical having 1 to 6 carbon atoms, optionally being halogenated; and/or the R$_3$ radical represents a radical of the formula —C$_6$H$_{(5-y')}$—B$_{y'}$ where y'=1, 2 or 3; or a radical of the formula -A-C$_6$H$_{(5-y)}$-By where y=0, 1 or 2; and/or the A radical of $R_3$ is a linear or branched, saturated or unsaturated hydrocarbon divalent radical having 1 to 12 carbon atoms, optionally substituted; and/or the B radical of $R_3$ is a linear or branched, saturated or unsaturated hydrocarbon radical having 1 to 12 carbon atoms, optionally substituted; and/or A and/or for B are selected from the group consisting of halogen; —CN; —COOR, —$NO_2$; and —$SO_2$—OR; with R representing a linear, branched or cyclic, saturated or unsaturated hydrocarbon radical having 1 to 6 carbon atoms, optionally being halogenated, and/or the X radical represents —OH or —OR4 with $R_4$ representing a linear, cyclic or branched, saturated or unsaturated hydrocarbon radical having 1 to 6 carbon atoms, optionally substituted, and/or $R_4$ of X is —OH or —OR with R representing a linear, cyclic or branched, saturated or unsaturated hydrocarbon radical having 1 to 6 carbon atoms, optionally being substituted.

3. A composition according to claim 1, wherein the compound of the formula (I) is such that:

the $R_1$ radical represents a methyl, ethyl, propyl or isopropyl radical, optionally substituted by a —OH or —P(O)—$(OH)_2$ group with R representing methyl, ethyl, propyl or isopropyl; and/or the $R_2$ radical represents a methyl, ethyl, propyl, isopropyl, n-butyl, ter-butyl or isobutyl radical; and/or the $R_3$ radical represents a group of one of the following formulae:

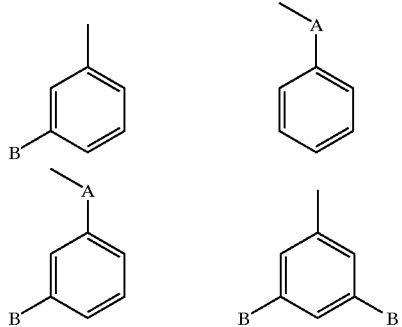

where the divalent A radical is a methylene, ethylene, propylene and/or the B radical is a methyl, ethyl, propyl or isopropyl radical, substituted by one or more halogens, and the X radical represents a radical selected from the group consisting of —OH, —$OCH_3$, —$OC_2H_5$, —O—$C_3H_7$ and —$OC_4H9$.

4. A composition according to claim 1, wherein the elastase inhibitor is selected from the group consisting of:
{2-[acetyl-(3-trifluoromethyl-phenyl)-amino]-3-methyl-butyrylamino}acetic acid,
{2-[acetyl-(3-trifluoromethyl-phenyl)-amino]-3-methyl-butyrylamino}ethyl acetate,
[2-(acetyl-benzyl-amino)-3-methyl-butyrylamino]acetic acid,
[2-(acetyl-benzyl-amino)-3-methyl-butyrylamino]ethyl acetate, and
(2-{benzyl-[(diethoxy-phosphoryl)-acetyl]-amino}-3-methyl-butyryl-amino]ethyl acetate.

5. A composition according to claim 1, wherein the elastase inhibitor is present in an amount ranging from 0.00001 to 20% by weight based on the total weight of the composition.

6. A composition according to claim 5, wherein the elastase inhibitor is present in an amount ranging from 0.00001 to 5% by weight.

7. A composition according to claim 1, wherein the metalloproteinase inhibitor is an inhibitor of the activity and/or the expression and/or the synthesis of metalloproteinases selected from the group consisting of MMP-1, MMP-2, MMP-3, MMP-7, MMP-9, MMP-11, MMP-12, MMP-13, MMP-14, MMP-15, MMP-16 and MMP-17.

8. A composition according to claim 1, wherein the metalloproteinase inhibitor is a tissue inhibitor of metalloproteinases.

9. A composition according to claim 1, wherein the metalloproteinase inhibitor is a tissue inhibitor of at least one of TIMP-1, TIMP-2, TIMP-3 and TIMP4.

10. A composition according to claim 1, wherein the metalloproteinase inhibitor is of natural origin.

11. A composition according to claim 1, wherein the metalloproteinase inhibitor represents from $10^{-12}$ to 5% of the total weight of the composition.

12. A composition according to claim 1, wherein the metalloproteinase inhibitor represents from $10^{-10}$ to 2% of the total weight of the composition.

13. A composition according to claim 1, comprising an effective amount of said N-acylaminoamide elastase inhibitor and said at least one metalloproteinase inhibitor to care for and/or treat ulcerated areas of the skin or areas of the skin having been subjected to a cutaneous stress or microstress.

14. A composition according to claim 1, in a form selected from the group consisting of:
a care, treatment, cleaning or protection product, of the face, scalp or body skin;
a sun protective, artificial sun tanning (self-tanning) or after-sun care composition;
a capillary composition;
a face skin, body or lip make-up product; and
a mouth hygiene product.

15. A composition according to claim 1, in the form of an anti-wrinkle, anti-ageing, sun protective or after-sun composition for the face.

16. A composition as claimed in claim 1, wherein said composition is a cosmetic, dermatological, or cosmetic and dermatological composition.

17. A composition according to claim 1, wherein the metalloproteinase inhibitor is of synthetic origin.

18. A composition according to claim 2, wherein the $R_1$ radical represents hydrogen or a linear or branched, saturated or unsaturated hydrocarbon radical having 1, 2, 3, 4, 5 or 6 carbon atoms, optionally substituted, and/or
the $R_2$ radical represents a linear, branched or cyclic, saturated or unsaturated hydrocarbon radical having 1, 2, 3, 4, 5 or 6 carbon atoms, optionally substituted.

19. A composition comprising an N-acylaminoamide elastase inhibitor and at least one metalloproteinase inhibitor, wherein the N-acylaminoamide elastase inhibitor is a compound of the formula (I):

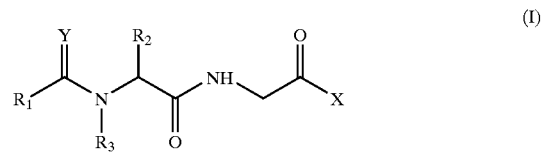

where
the Y radical represents oxygen, the R₁ radical represents hydrogen or a linear or branched, saturated or unsaturated hydrocarbon radical having 1 to 12, optionally substituted, the R1 substituents being selected from the group consisting of —OH; —OR; and —P(O)—(OR)₂ with R representing a linear, branched or cyclic, saturated or unsaturated hydrocarbon radical having 1 to 6 carbon atoms, optionally being halogenated;

the R₂ radical represents a linear, branched or cyclic, saturated or unsaturated hydrocarbon radical having 1 to 12 carbon atoms, optionally substituted, the R₂ substituents being —OH or —OR with R representing a linear, branched or cyclic, saturated or unsaturated hydrocarbon radical having 1 to 6 carbon atoms, optionally being halogenated;

the R₃ radical represents a radical of the formula —C₆H₍₅₋y'₎—B_{y'}, where y'=1, 2 or 3; or a radical of the formula -A-C₆H₍₅₋y₎-By where y=0, 1 or 2;

the A radical of R₃ is a linear or branched, saturated or unsaturated hydrocarbon divalent radical having 1 to 12 carbon atoms, optionally substituted;

the B radical of R₃ is a linear or branched, saturated or unsaturated hydrocarbon radical having 1 to 12 carbon atoms, optionally substituted;

A and/or for B are selected from the group consisting of -halogen; —CN; —COOR; —NO₂; and —SO₂—OR; with R representing a linear, branched or cyclic, saturated or unsaturated hydrocarbon radical having 1 to 6 carbon atoms, optionally being halogenated, and/or the X radical represents —OH or —OR4 with R₄ representing a linear, cyclic or branched, saturated or unsaturated hydrocarbon radical having 1 to 6 carbon atoms, optionally substituted, and R₄ of X is —OH or —OR with R representing a linear, cyclic or branched, saturated or unsaturated hydrocarbon radical having 1 to 6 carbon atoms, optionally being substituted.

20. A composition comprising an N-acylaminoamide elastase inhibitor and at least one metalloproteinase inhibitor, wherein the N-acylaminoamide elastase inhibitor is a compound of the formula (I):

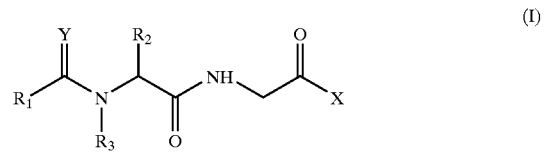

(I)

where the R₁ radical represents a methyl, ethyl, propyl or isopropyl radical, optionally substituted by a —OH or —P(O)—(OR)₂ group with R representing methyl, ethyl, propyl or isopropyl;

the R₂ radical represents a methyl, ethyl, propyl, isopropyl, n-butyl, ter-butyl or isobutyl radical;

the R₃ radical represents a group of one of the following formulae:

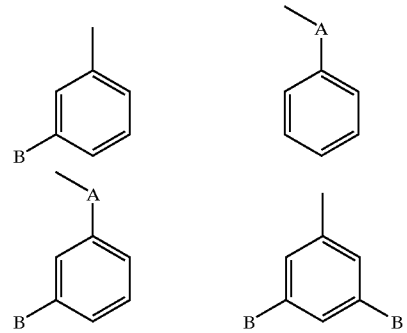

where the divalent A radical is a methylene, ethylene, propylene and/or the B radical is a methyl, ethyl, propyl or isopropyl radical, substituted by one or more halogens, and the X radical represents a radical selected from the group consisting of —OH, —OCH₃, —OC₂H₅, —O—C₃H₇ and —OC₄H₉.

* * * * *